(12) United States Patent
Kawamura

(10) Patent No.: US 10,743,833 B2
(45) Date of Patent: *Aug. 18, 2020

(54) RADIOGRAPHIC IMAGE PROCESSING APPARATUS, METHOD AND RECORDING MEDIUM

(71) Applicant: FUJIFILM Corporation, Tokyo (JP)

(72) Inventor: Takahiro Kawamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

This patent is subject to a terminal disclaimer.

(21) Appl. No.: 16/110,209

(22) Filed: Aug. 23, 2018

(65) Prior Publication Data

US 2019/0008473 A1 Jan. 10, 2019

Related U.S. Application Data

(62) Division of application No. 15/270,085, filed on Sep. 20, 2016, now Pat. No. 10,080,541.

(30) Foreign Application Priority Data

Sep. 24, 2015 (JP) ................................ 2015-186580

(51) Int. Cl.
*H05G 1/28* (2006.01)
*A61B 6/00* (2006.01)

(52) U.S. Cl.
CPC .............. *A61B 6/58* (2013.01); *A61B 6/4216* (2013.01); *A61B 6/4405* (2013.01); *A61B 6/461* (2013.01);

(Continued)

(58) Field of Classification Search
CPC .. A61B 6/00; A61B 6/58; A61B 6/588; A61B 6/5282; A61B 6/482; A61B 6/461;
(Continued)

(56) References Cited

U.S. PATENT DOCUMENTS

| 4,945,552 A * | 7/1990 | Ueda .......................... G01T 1/36 378/156 |
| 10,080,541 B2 * | 9/2018 | Kawamura .............. A61B 6/58 |

(Continued)

FOREIGN PATENT DOCUMENTS

| JP | 2014-207958 A | 11/2014 |
| JP | 2015-43959 A | 3/2015 |

*Primary Examiner* — Jurie Yun
(74) *Attorney, Agent, or Firm* — Sughrue Mion, PLLC

(57) ABSTRACT

An image obtainment unit obtains plural radiographic-images generated by arranging plural storable-phosphor-sheets in such a manner that at least portions of the sheets are overlapped with each other in an irradiation direction of radiation, by arranging a marker at a position to be detected by the plural sheets, and by detecting the radiation that has passed through a subject and the marker by each of the plural sheets. A first-information obtainment unit obtains first-information representing a distance between detection surfaces of the plural sheets. A second-information obtainment unit obtains second-information representing a magnification ratio of a second marker image of the marker included in a radiographic-image obtained by a second sheet with respect to a marker image of the marker included in a radiographic-image obtained by a first sheet of the plural sheets. A distance calculation unit calculates, based on the first and the second information, a radiation-source-to-image-surface distance.

4 Claims, 6 Drawing Sheets

(52) U.S. Cl.
CPC ............ *A61B 6/482* (2013.01); *A61B 6/5282* (2013.01); *A61B 6/588* (2013.01)

(58) Field of Classification Search
CPC .. A61B 6/4405; A61B 6/4216; G01N 23/087; G06T 2211/408; H04N 5/3205; H04N 5/325; G01R 33/56
USPC ...... 378/62, 162, 163, 98.9, 98.11; 382/130, 382/132
See application file for complete search history.

(56) References Cited

U.S. PATENT DOCUMENTS

| | | |
|---|---|---|
| 2015/0379711 A1 | 12/2015 | Imai |
| 2016/0140720 A1 | 5/2016 | Naito |

* cited by examiner

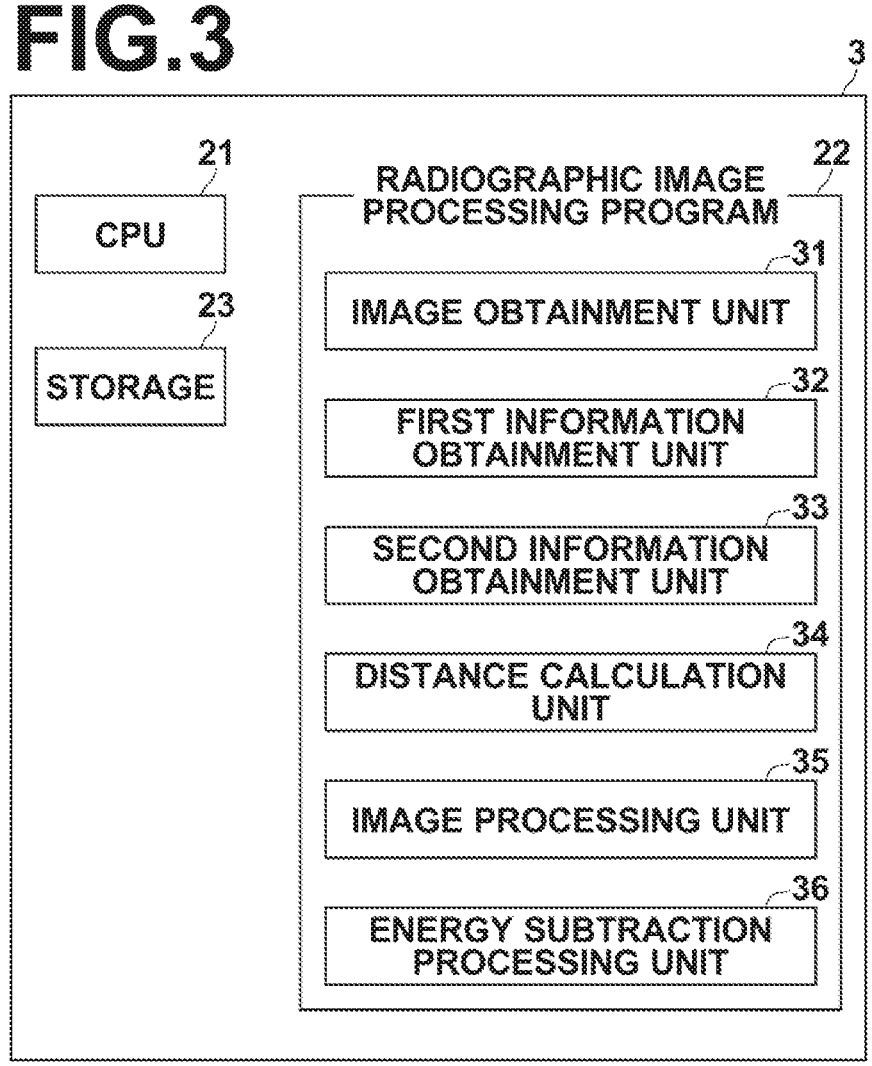

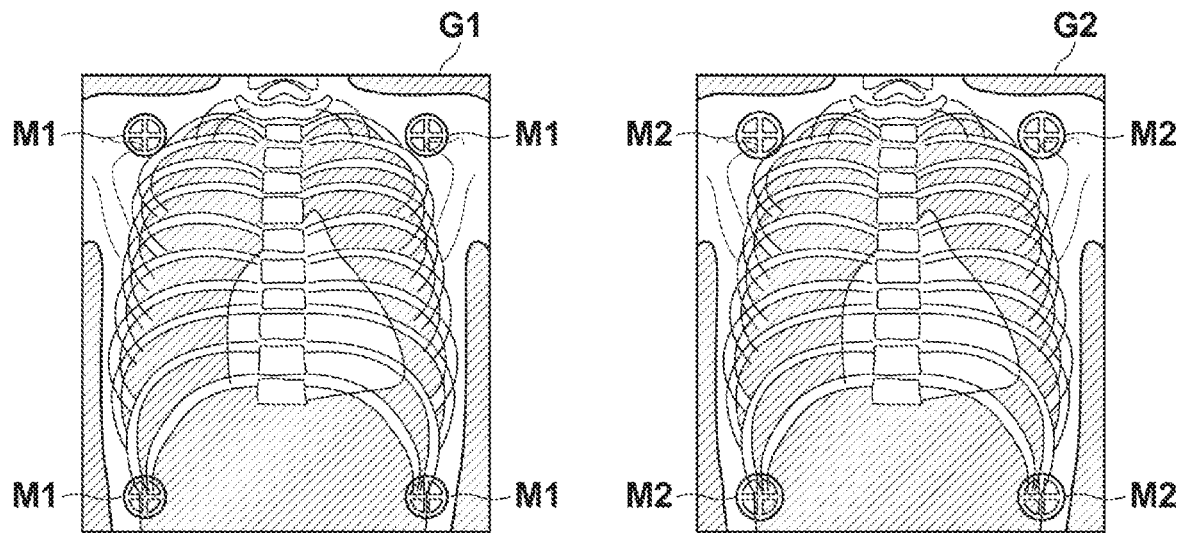
FIG.4A  FIG.4B
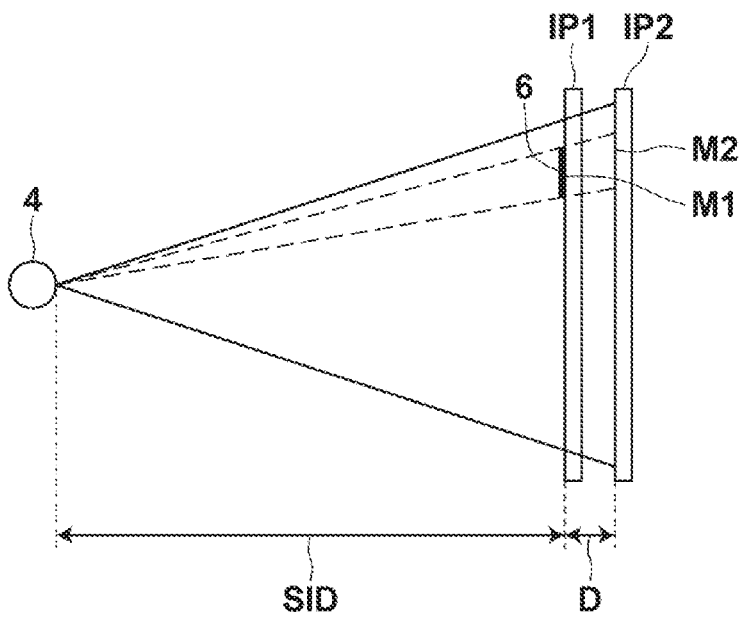
FIG.5

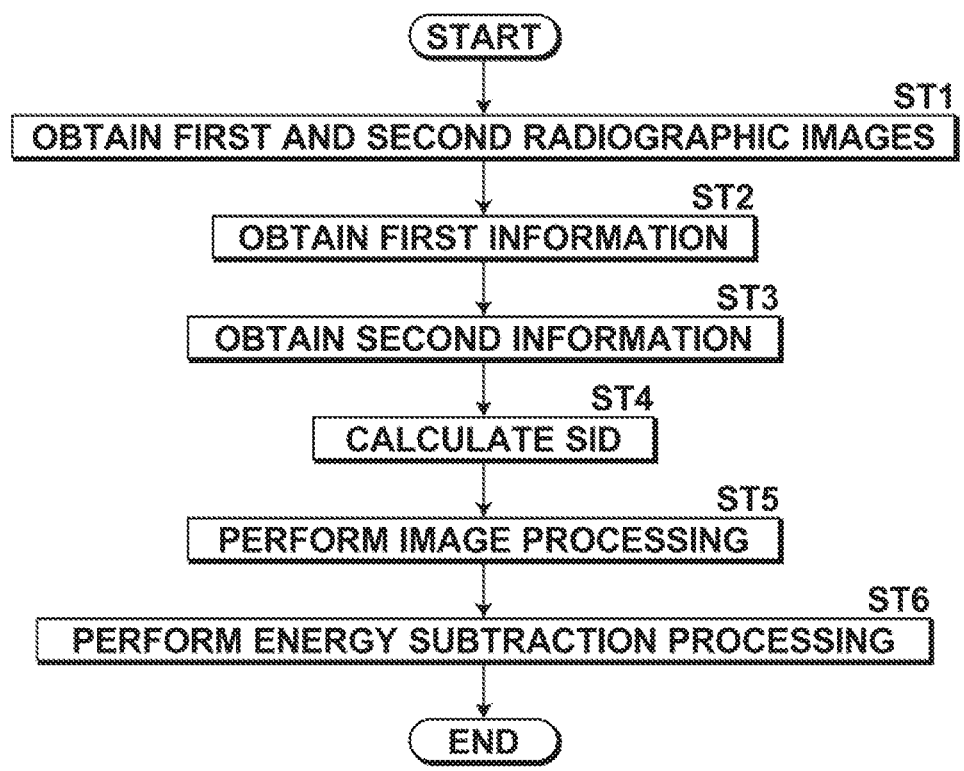
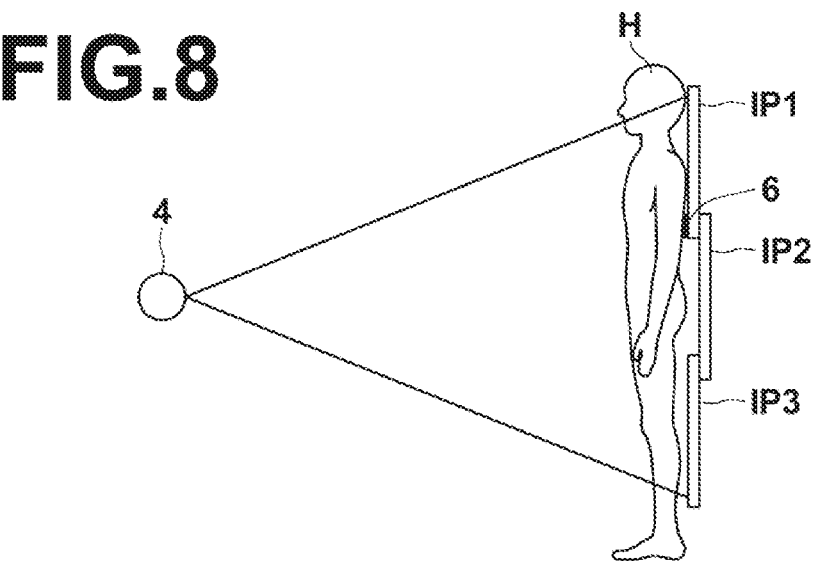

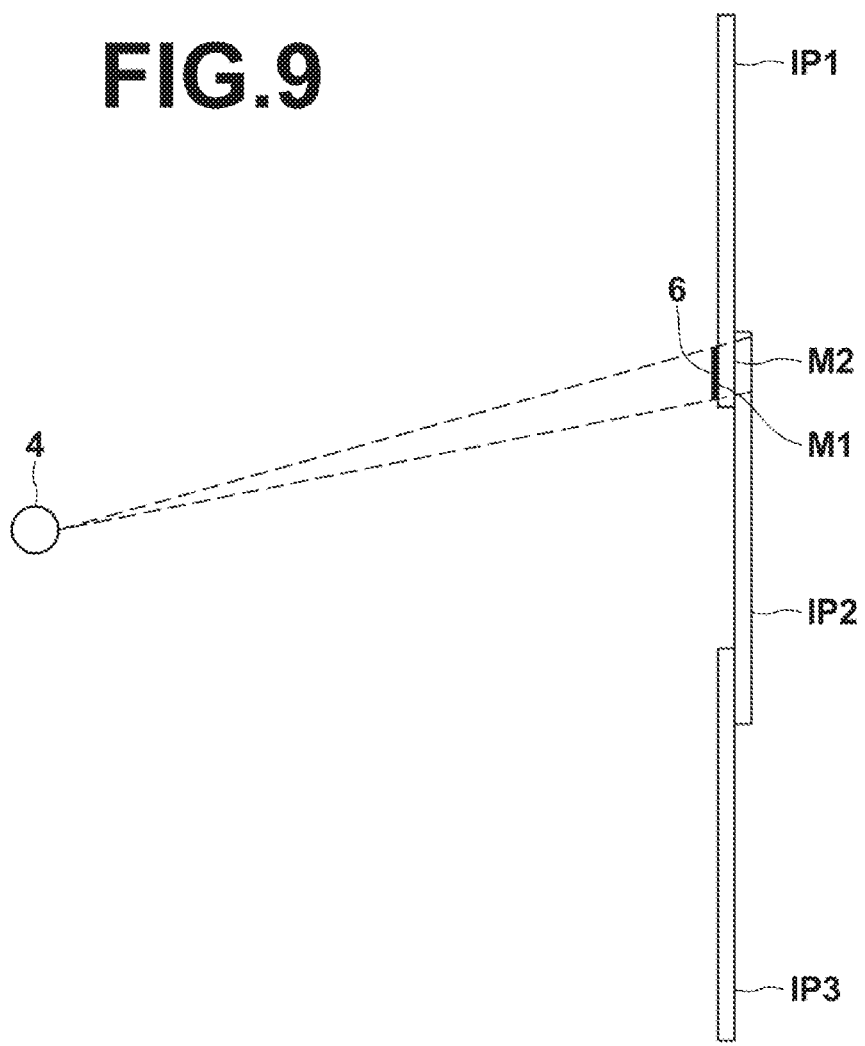

RADIOGRAPHIC IMAGE PROCESSING APPARATUS, METHOD AND RECORDING MEDIUM

CROSS-REFERENCE TO RELATED APPLICATION

The present application is a divisional application of U.S. application Ser. No. 15/270,085, filed Sep. 20, 2016, which claims priority under 35 U.S.C. § 119 to Japanese Patent Application No. 2015-186580, filed on Sep. 24, 2015. The above applications are hereby expressly incorporated by reference, in their entirety, into the present application.

BACKGROUND

The present disclosure relates to a radiation-source-to-image-surface distance obtainment apparatus, method and program that obtains a radiation-source-to-image-surface distance, which is a distance between a radiation source that outputs radiation to a subject and a detection surface of a detection means that detects radiation that has passed through a subject. Further, the present disclosure relates to a radiographic image processing apparatus, method and program that performs image processing on a radiographic image by using the radiation-source-to-image-surface distance.

Conventionally, in performing radiography on a subject by radiation passed through the subject, there is a problem that radiation is scattered in the subject, and this scattered radiation (hereinafter, referred to as scattered radiation) lowers the contrast of an obtainable radiographic image. Therefore, radiography is performed, in some cases, by arranging a scattered radiation removal grid (hereinafter, simply referred to as a grid) between a subject and a detection means, such as a radiation detector for obtaining a radiographic image by detecting radiation, so that the detection means is not irradiated with the scattered radiation. If radiography is performed by using the grid, the detection means tends not to be irradiated with radiation scattered by the subject. Therefore, it is possible to improve the contrast of the radiographic image.

Meanwhile, if radiography is performed by using a grid, a stripe pattern (grid stripe) corresponding to the grid is included in a radiographic image together with a subject image, and observation of the image becomes difficult. Therefore, scattered radiation removal processing in which radiography is performed without using a grid, and an effect of improving image quality that would be achievable by removal of scattered radiation by a grid is given to the radiographic image by image processing has been proposed (please refer to Japanese Unexamined Patent Publication No. 2014-207958 (Patent Document 1) and Japanese Unexamined Patent Publication No. 2015-043959 (Patent Document 2)). Patent Document 1 proposes a technique for performing scattered radiation removal processing based on virtual grid characteristics, in which a virtual grid is assumed. Further, Patent Document 2 proposes a technique for performing scattered radiation removal processing by estimating the body thickness of a subject.

Further, in recent years, so-called portable radiography, which uses a portable-type radiation irradiation apparatus and a portable-type detection means, has been performed. The weight of a radiation irradiation apparatus for performing portable radiography has been reduced to such a degree that an operator can operate the radiation irradiation apparatus held by his/her hand or hands, and it is easy to carry the radiation irradiation apparatus. Therefore, radiography of a subject is possible at various locations, for example, such as a patient's room in a hospital and a natural disaster site.

SUMMARY

Meanwhile, a radiation-source-to-image-surface distance, i.e. an SID (Source to Image Distance), which is a distance between a radiation source and a detection surface of a detection means, is needed to perform image processing, such as the aforementioned scattered radiation removal processing. The SID is easily obtainable at a location, such as a radiography room, in which a radiation source and a detection means are installed at fixed positions. Therefore, accurate image processing is possible by using the obtained SID.

However, in the aforementioned portable radiography, a radiation irradiation apparatus is used in a state of being held by a hand or hands. Further, a detection means is arranged on the rear side of a subject. Therefore, it is difficult to obtain an accurate SID. In this case, an SID may be measured by visual observation, and the obtained value may be used for image processing. However, since the SID measured by visual observation is not an accurate value, it is impossible to accurately perform image processing. Further, a sensor or the like for measuring the SID may be provided in the radiation irradiation apparatus. However, if such a sensor or the like is provided, the configuration of the apparatus becomes complex, and also the cost of the apparatus becomes higher.

In view of the foregoing circumstances, the present disclosure is directed to make it possible to obtain an accurate SID.

Further, the present disclosure is directed to accurately perform image processing by using the SID.

A radiation-source-to-image-surface distance obtainment apparatus of the present disclosure includes an image obtainment means that obtains plural radiographic images generated by arranging plural detection means that detect radiation that has been output from a radiation source and passed through a subject in such a manner that at least portions of the plural detection means are overlapped with each other in an irradiation direction of the radiation, and by arranging at least one marker at a position to be detected by the plural detection means, and by detecting the radiation that has passed through the subject and the marker by each of the plural detection means, a first information obtainment means that obtains first information representing a distance between a detection surface of a first detection means located closest to the radiation source among the plural detection means and a detection surface of a second detection means other than the first detection means among the plural detection means, a second information obtainment means that obtains second information representing a magnification ratio of a second marker image of the at least one marker included in a second radiographic image obtained by the second detection means with respect to a first marker image of the at least one marker included in a first radiographic image obtained by the first detection means and a distance calculation means that calculates, based on the first information and the second information, a radiation-source-to-image-surface distance, which is a distance between the radiation source and the detection surface of the first detection means.

As the "detection means", a storable phosphor sheet as well as a radiation detector may be used. The storable phosphor sheet utilizes storable phosphor, which stores a part of radiation energy by being irradiated with radiation, and after then, outputs stimulated emission light corresponding to the stored radiation energy by being irradiated with excitation light, such as visible light and a laser beam. In the case that the detection means is a radiation detector, the image obtainment means should obtain a radiographic image represented by image signals output from the radiation detector. In the case that the detection means is a storable phosphor sheet, a radiography apparatus is used, and radiographic image information is temporarily stored and recorded on a storable phosphor sheet by irradiation of the storable phosphor sheet with radiation that has passed through a subject. Further, an image readout apparatus is used, and stimulated emission light is induced by irradiation of this storable phosphor sheet with excitation light, and image signals representing a radiographic image is generated by performing photoelectric conversion on the stimulated emission light. Therefore, the image obtainment means should obtain a radiographic image represented by image signals generated in this manner.

The expression "arranging plural detection means in such a manner that at least portions of the plural detection means are overlapped with each other in an irradiation direction of the radiation" means that detection surfaces of the plural detection means are arranged perpendicular to an optical axis of radiation output from a radiation source, and that at least portions of the plural detection means are overlapped with each other. In this case, the plural detection means may be in close contact with each other or spaced apart from each other at the overlapped portions. Further, the expression "arranging in such a manner that at least portions of the plural detection means are overlapped with each other" includes both of a case in which the plural detection means are arranged in such a manner that the entire areas of the plural detection means are overlapped with each other and a case, such as long-size radiography, in which the plural detection means are arranged in such a manner that portions of the plural detection means are overlapped with each other.

The "marker" has a shape extending in the surface direction of the detection means. For example, the marker may have a cross shape of intersecting segments. Further, the marker is made of arbitrary material that is able to make a marker image, which is an image of the marker, included in a radiographic image in such a manner to be distinguishable from a subject image. In the case that a contrast between the tissue of the subject and the marker is considered, it is desirable that the marker is made of material, such as metal that does not pass radiation. Here, it is desirable that the marker is in close contact with the detection surface of the first detection means. However, the marker may be arranged away from the detection surface of the first detection means.

In the radiation-source-to-image-surface distance obtainment apparatus of the present disclosure, in the case that the arranged at least one marker is plural markers, the second information obtainment means may obtain, as the second information, an average value of the magnification ratio obtained for each marker.

A radiographic image processing apparatus of the present disclosure includes the radiation-source-to-image-surface distance obtainment apparatus of the present disclosure, and an image processing means that performs image processing on at least one of the plural radiographic images by using the radiation-source-to-image-surface distance obtained by the radiation-source-to-image-surface distance obtainment apparatus.

In the radiographic image processing apparatus of the present disclosure, the image processing means may perform scattered radiation removal processing, as the image processing.

A radiation-source-to-image-surface distance obtainment method of the present disclosure includes obtaining plural radiographic images generated by arranging plural detection means that detect radiation that has been output from a radiation source and passed through a subject in such a manner that at least portions of the plural detection means are overlapped with each other in an irradiation direction of the radiation, and by arranging at least one marker at a position to be detected by the plural detection means, and by detecting the radiation that has passed through the subject and the marker by each of the plural detection means, obtaining first information representing a distance between a detection surface of a first detection means located closest to the radiation source among the plural detection means and a detection surface of a second detection means other than the first detection means among the plural detection means, obtaining second information representing a magnification ratio of a second marker image of the at least one marker included in a second radiographic image obtained by the second detection means with respect to a first marker image of the at least one marker included in a first radiographic image obtained by the first detection means, and calculating, based on the first information and the second information, a radiation-source-to-image-surface distance, which is a distance between the radiation source and the detection surface of the first detection means.

A radiographic image processing method of the present disclosure includes obtaining the radiation-source-to-image-surface distance by using the radiation-source-to-image-surface distance obtainment method of the present disclosure, and performing image processing on at least one of the plural radiographic images by using the radiation-source-to-image-surface distance.

Here, the radiation-source-to-image-surface distance obtainment method and the radiographic image processing method of the present disclosure may be provided as programs to be executed by a computer.

According to the present disclosure, first information representing a distance between a detection surface of a first detection means located closest to the radiation source among plural detection means and a detection surface of a second detection means other than the first detection means among the plural detection means is obtained. Further, second information representing a magnification ratio of a second marker image of at least one marker included in a second radiographic image obtained by the second detection means with respect to a first marker image of the at least one marker included in a first radiographic image obtained by the first detection means is obtained. Further, a radiation-source-to-image-surface distance is calculated based on the first and second information. Therefore, it is possible to obtain an accurate radiation-source-to-image-surface distance by using an apparatus of simple and low-cost configuration without providing a sensor and the like.

Further, image processing is performed on at least one of plural radiographic images by using the radiation-source-to-image-surface distance. Therefore, it is possible to perform highly accurate image processing by using the accurate radiation-source-to-image-surface distance.

BRIEF DESCRIPTION OF THE DRAWINGS

FIG. 3 is a schematic diagram illustrating the configuration of a radiographic image processing apparatus realized by installing a radiographic image processing program in a computer;

FIG. 4A is a diagram illustrating a first radiographic image;

FIG. 4B is a diagram illustrating a second radiographic image;

FIG. 5 is a diagram for explaining calculation of an SID in energy subtraction radiography;

FIG. 7 is a flow chart showing processing performed in embodiments of the present disclosure;

FIG. 8 is a diagram for explaining long-size radiography; and

FIG. 9 is a diagram for explaining calculation of an SID in long-size radiography.

DETAILED DESCRIPTION OF THE PREFERRED EMBODIMENTS

Figure 1:
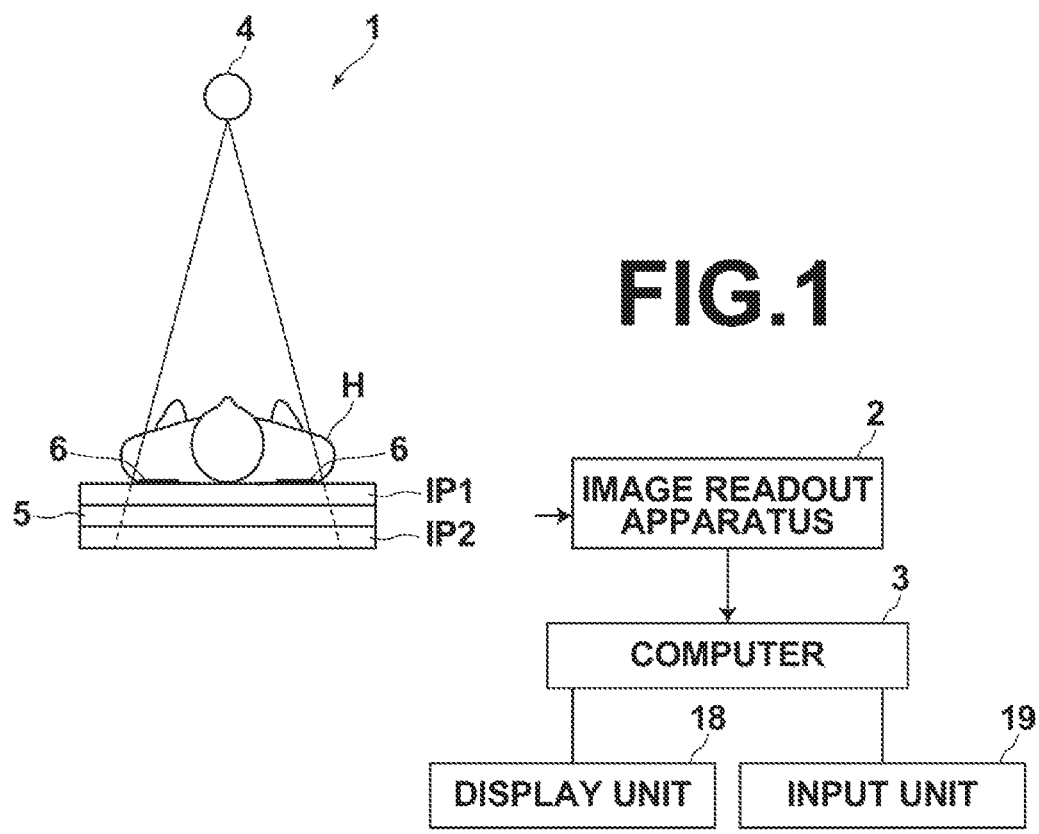
FIG. 1 is a schematic block diagram illustrating the configuration of a radiography system to which a radiationsource-to-image-surface distance obtainment apparatus and a radiographic image processing apparatus according to embodiments of the present disclosure have been applied.

Hereinafter, embodiments of the present disclosure will be described with reference to drawings. FIG. 1 is a schematic block diagram illustrating the configuration of a radiography system to which a radiation-source-to-image-surface distance obtainment apparatus and a radiographic image processing apparatus according to embodiments of the present disclosure have been applied. As illustrated in FIG. 1, the radiography system according to embodiments of the present disclosure is a system for radiographing a radiographic image of subject H and performing, on the radiographic image, various kinds of image processing including scattered radiation removal processing. The radiography system includes a radiography apparatus 1, an image readout apparatus 2, and a computer 3 including a radiation-source-to-image-surface distance obtainment apparatus and a radiographic image processing apparatus according to embodiments of the present disclosure.

The radiography apparatus 1 is a radiography apparatus for performing so-called one-shot energy subtraction, in which two storable phosphor sheets IP1, IP2 are irradiated, at different energy from each other, with X-rays that have been output from an X-ray source 4, which is a radiation source, and passed through subject H. When radiography is performed, first storable phosphor sheet IP1 and second storable phosphor sheet IP2 are arranged in this order from a side closer to the X-ray source 4, as illustrated in FIG. 1. Further, a filter 5 for X-ray energy conversion, which is composed of a copper plate, is arranged between these two sheets IP1, IP2, and the X-ray source 4 is driven. Here, storable phosphor sheets IP1, IP2 and the filter 5 for X-ray energy conversion are in close contact with each other.

Accordingly, first storable phosphor sheet IP1 stores and records radiographic image information about subject H by low-voltage X-rays, which also include so-called soft radiation, and second storable phosphor sheet IP2 stores and records radiographic image information about subject H by high-voltage X-rays after the soft radiation has been removed. At this time, the positional relationship of subject H with storable phosphor sheet IP1 is the same as the positional relationship of subject H with storable phosphor sheet IP2. Accordingly, radiographic image information in which at least a part of image information about subject H is different from each other is stored and recorded in two storable phosphor sheets IP1, IP2. Meanwhile, in the present embodiment, plural markers 6 made of metal, such as lead, that does not pass X-rays are arranged on a detection surface of first storable phosphor sheet IP1. Here, storable phosphor sheets IP1, IP2 correspond to detection means.

Figure 2:
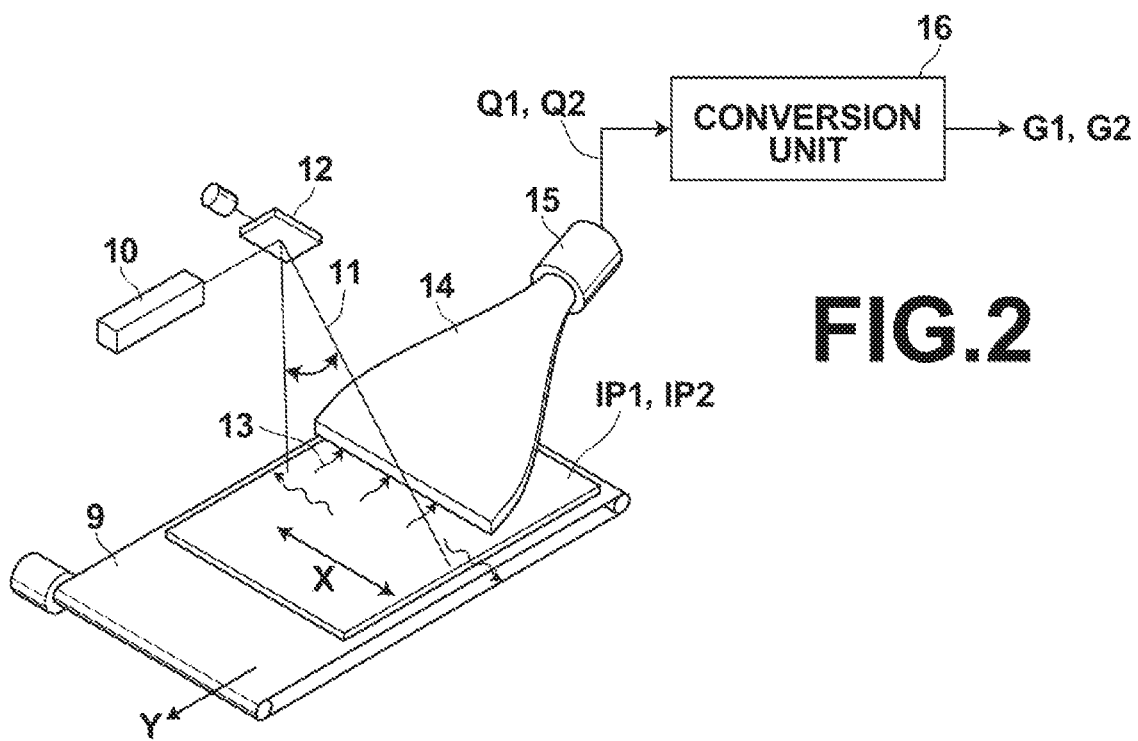
FIG. 2 is a schematic diagram illustrating the configuration of an image readout apparatus.

FIG. 2 is a schematic diagram illustrating the configuration of an image readout apparatus. First, while storable phosphor sheet IP1 of storable phosphor sheets IP1 IP2, in which radiographic image information has been stored and recorded as described above, is moved by an endless belt 9 in the direction of arrow Y, main scan is performed in X direction on sheet IP1 with excitation light 11, which is a laser beam from a laser light source 10, by deflecting the excitation light 11 by a scan mirror 12. Stimulated emission light 13 of a light amount corresponding to radiographic image information stored and recorded in storable phosphor sheet IP1 is emitted from storable phosphor sheet IP1 by scan with the excitation light. The stimulated emission light 13 enters the inside of a light guide 14 from an end surface of the light guide 14 produced by forming a transparent acrylic plate, and travels in the inside of the light guide 14 while repeating total reflection, and is received by a photomultiplier 15. The photomultiplier 15 outputs analog output signal Q1 corresponding to the light emission amount of the stimulated emission light 13, in other words, representing radiographic image information about subject H.

A conversion unit 16 performs logarithmic transformation on output signal Q1, and further A/D conversion on the signal after logarithmic transformation. Accordingly, output signal Q1 is converted to digital first radiographic image G1. Next, output signal Q2 is obtained by reading out image information recorded in the other storable phosphor sheet IP2, and the conversion unit 16 converts output signal Q2 to digital second radiographic image G2 exactly in a similar manner. First and second radiographic images G1, G2 are input to the computer 3.

A display unit 18 and an input unit 19 are connected to the computer 3. The display unit 18 includes a CRT (Cathode Ray Tube), a liquid crystal display or the like, and displays a radiographic image obtained by radiography, and assists a user in various kinds of input necessary for processing performed in the computer 3. The input unit 19 includes a keyboard, a mouse, a touch panel or the like.

A radiation-source-to-image-surface distance obtainment program and a radiographic image processing program according to the embodiments of the present disclosure have been installed in the computer 3. Since the radiation-source-to-image-surface distance obtainment program is included in the radiographic image processing program, the radiation-source-to-image-surface distance obtainment program and the radiographic image processing program will be simply referred to hereafter as the radiographic image processing program. In the embodiments of the present disclosure, a computer may be a workstation or a personal computer directly operated by an operator, or a server computer connected to them through a network. The radiographic image processing program is recorded in a recording medium, such as a DVD (Digital Versatile Disc) and a CD-ROM (Compact Disc Read Only Memory), and distributed, and installed in a computer from the recording medium. Alternatively, the program is stored in a storage device of a server computer connected to a network or in a network storage in an accessible manner from the outside, and downloaded to a computer by a request, and installed.

FIG. 3 is a schematic diagram illustrating the configuration of a radiographic image processing apparatus realized by installing a radiographic image processing program in the computer 3. As illustrated in FIG. 3, the radiographic image processing apparatus includes, as standard computer configuration, a CPU (Central Processing Unit) 21, a memory 22, and a storage 23.

The storage 23 includes a storage device, such as a hard disk and an SSD (Solid State Drive). Various kinds of information including a program for driving each unit of the radiography apparatus 1 and the radiographic image processing program have been stored in the storage 23. Further, radiographic images obtained by radiography are also stored in the storage 23. Further, various kinds of table that will be described later are stored in the storage 23.

A program stored in the storage 23, or the like is temporarily stored in the memory 22 to cause the CPU 21 to perform various kinds of processing. The radiographic image processing program defines, as processing to be performed by the CPU 21, image obtainment processing for obtaining first and second radiographic images G1, G2, first information obtainment processing for obtaining first information representing a distance between a detection surface of first storable phosphor sheet IP1 located closest to the X-ray source 4 and a detection surface of second storable phosphor sheet IP2, second information obtainment processing for obtaining second information representing a magnification ratio of a second marker image of a marker 6 included in second radiographic image G2 obtained by second storable phosphor sheet IP2 with respect to a first marker image of the marker 6 included in first radiographic image G1 obtained by first storable phosphor sheet IP1, distance calculation processing for calculating, based on the first and second information, an SID, which is a distance between the X-ray source 4 and first storable phosphor sheet IP1, image processing on radiographic images G1, G2 by using the SID, and energy subtraction processing on processed radiographic images G1, G2.

The CPU 21 performs these kinds of processing based on the radiographic image processing program, and thereby the computer 3 functions as an image obtainment unit 31, a first information obtainment unit 32, a second information obtainment unit 33, a distance calculation unit 34, an image processing unit 35, and an energy subtraction processing unit 36. Here, the computer 3 may include processors for performing image obtainment processing, first information obtainment processing, second information obtainment processing, distance calculation processing, image processing, and energy subtraction processing, respectively. Here, storable phosphor sheets IP1, IP2 correspond to first and second detection means, respectively. Further, the image obtainment unit 31, the first information obtainment unit 32, the second information obtainment unit 33, and the distance calculation unit 34 constitute a source-to-image distance obtainment apparatus of the present disclosure.

The image obtainment unit 31 obtains first and second radiographic images G1, G2 generated by the image readout apparatus 2, and stores first and second radiographic images G1, G2 in the storage 23. Here, in the case that first and second radiographic images G1, G2 have been stored in another storage device, such as a server, first and second radiographic images G1, G2 should be obtained from the storage device.

The first information obtainment unit 32 obtains first information J1 representing distance D between a detection surface of first storable phosphor sheet IP1 and a detection surface of second storable phosphor sheet IP2. Here, since the thicknesses of first and second storable phosphor sheets IP1, IP2 and the thickness of the filter 5 are already known, distance D is a value obtained by adding the thickness of the filter 5 to the thickness of first storable phosphor sheet IP1. The first information obtainment unit 32 obtains first information J1 representing distance D by receiving an input by an operator from the input unit 19. Alternatively, first information J1 may have been stored in the storage 23 in advance. In this case, the first information obtainment unit 32 obtains first information J1 by reading out first information J1 from the storage 23.

The second information obtainment unit 33 obtains second information J2 representing a magnification ratio of a second marker image of a marker 6 included in second radiographic image G2, obtained by second storable phosphor sheet IP2, with respect to a first marker image of the marker 6 included in first radiographic image G1, obtained by first storable phosphor sheet IP1. FIGS. 4A and 4B are diagrams illustrating first and second radiographic images G1, G2. As illustrated in FIGS. 4A and 4B, first and second radiographic images G1, G2 include image information about subject H and plural marker images M1, M2 of the markers 6. Here, the marker has a shape in which a circular frame and cross-shaped intersecting segments are combined together.

Meanwhile, X-rays output from the X-ray source 4 are cone beams. Therefore, the size of second marker image M2 included in second radiographic image G2 is larger than the size of first marker image M1 included in first radiographic image G1. The second information obtainment unit 33 obtains, as second information J2, magnification ratio K of second marker image M2 with respect to first marker image M1. In the present embodiment, four markers 6 are used. Therefore, four first marker images M1 and four second marker images M2 are included in first and second radiographic image G1, G2, respectively. The second information obtainment unit 33 calculates four magnification ratios for the markers 6, respectively, and obtains, as second information J2, magnification ratio K that is a representative value, such as an average or a median of the four magnification ratios. Magnification ratio K is calculated by template matching between first marker image M1 and second marker image M2 corresponding to each other. Alternatively, a ratio of diameters of circular parts of first and second marker images M1, M2 in a predetermined direction may be used.

The distance calculation unit 34 calculates an SID based on first information J1 and second information J2. FIG. 5 is a diagram for explaining calculation of an SID. In FIG. 5, a broken line indicates a portion of X-rays output from the X-ray source 4 that irradiates the marker 6. The range of first marker image M1 is a range in which first storable phosphor sheet IP1 and the broken line portion of the X-rays cross each other. The range of second marker image M2 is a range in which second storable phosphor sheet IP2 and the broken line portion of the X-rays cross each other. Magnification ratio K that is second information J2 obtained by the second information obtainment unit 33 may be expressed by the following expression (1), using an SID and distance D between the detection surface of first storable phosphor sheet IP1 and the detection surface of second storable phosphor sheet IP2:

$$K=(SID+D)/SID \qquad (1).$$

Therefore, the SID is calculable by using the following expression (2), using distance D and magnification ratio K:

$$SID=D/(K-1) \qquad (2).$$

For example, in the case that D is 2 cm, and magnification ratio K is 1.01, the SID is 200 cm.

Figure 6:
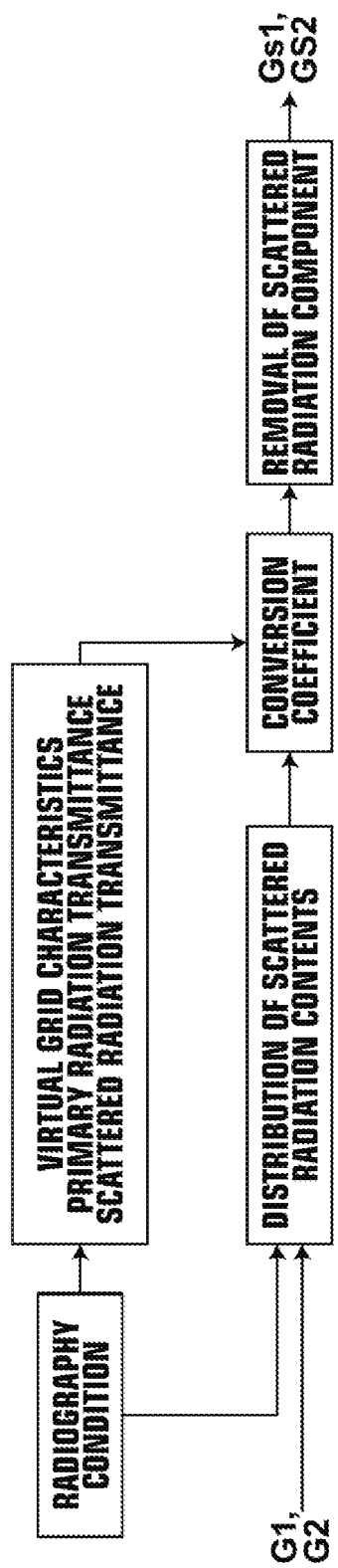
FIG. 6 is a block diagram illustrating scattered radiation removal processing.

The image processing unit 35 performs image processing on first and second radiographic image G1, G2 by using the SID. In the present embodiment, image processing including scattered radiation removal processing is performed. Next, scattered radiation removal processing will be described. FIG. 6 is a block diagram illustrating scattered radiation removal processing;

In the present embodiment, no grid is used during radiography. Therefore, the image processing unit 35 performs scattered radiation removal processing on first and second radiographic images G1, G2 to give a similar scattered radiation removal effect achievable if radiography is performed by actually using a grid. Scattered radiation removal processing is performed by using virtual grid characteristics the actual use of which is presumable, for example, as described in Patent Document 1. Therefore, the image processing unit 35 obtains virtual grid characteristics by an input by an operator from the input unit 19. In the present embodiment, the virtual grid characteristics are scattered radiation transmittance Ts about a virtual grid and transmittance of primary radiation irradiating first and second storable phosphor sheets IP1, IP2 after passing through subject H (primary radiation transmittance) Tp. Here, scattered radiation transmittance Ts and primary radiation transmittance Tp are values between 0 and 1.

The image processing unit 35 may obtain the virtual grid characteristics by directly receiving inputs of the values of scattered radiation transmittance Ts and primary radiation transmittance Tp. However, in the present embodiment, the virtual grid characteristics, i.e, scattered radiation transmittance Ts and primary radiation transmittance Tp are obtained by receiving an input of radiography conditions from the input unit 19 at the time of obtainment of a radiographic image.

Radiography conditions include an SID, the radiation dose of radiography, tube voltage, the material of a target of a radiation source and a filter, the kind of a storable phosphor sheet used in radiography, and the like. Here, in radiography of a radiographic image, the kind of a grid to be used has been generally determined based on radiography conditions, and scattered radiation transmittance Ts and primary radiation transmittance Tp are different based on the kind of the grid. Therefore, regarding radiography conditions, a table showing correspondence between various kinds of radiography conditions and virtual grid characteristics has been stored in the storage 23. Meanwhile, the various kinds of radiography conditions have been often determined based on facilities in which a radiography system is installed. Therefore, in the case that radiography conditions during actual radiography are unknown, radiography conditions based on the facilities should be used. The image processing unit 35 obtains, with reference to the table stored in the storage 23, virtual grid characteristics based on radiography conditions input from the input unit 19.

Further, the image processing unit 35 calculates, based on the following expressions (3), (4), a primary radiation image and a scattered radiation image from distribution T(x, y) of the thickness of a subject in radiographic images G1, G2. Then, the image processing unit 35 calculates, based on expression (5), distribution S (x, y) of scattered radiation contents from the calculated primary radiation image and scattered radiation image:

$$Icp(x,y)=Io(x,y)\times\exp(-\mu\times T(x,y)) \quad (3);$$

$$Ics(x,y)=Io(x,y)*S\sigma(T(x,y)) \quad (4); \text{ and}$$

$$S(x,y)=Ics(x,y)/(Ics(x,y)+Icp(x,y)) \quad (5),$$

where (x, y) is the coordinate of a pixel position of projection image Gi,

Icp(x, y) is a primary radiation image at pixel position (x, y),

Ics(x, y) is a scattered radiation image at pixel position (x, y),

Io(x, y) is an incident radiation dose onto a subject surface at pixel position (x, y), μ is a radiation attenuation coefficient of subject H, and Sσ(T(x, y)) is convolution kernel representing the characteristics of scatter based on the thickness of a subject at pixel position (x, y).

Further, distribution T(x, y) of the thickness of a subject should be calculated by assuming that the distribution of brightness in first and second radiographic images G1, G2 substantially coincides with the distribution of the thickness of a subject, and by converting pixel values of first and second radiographic images G1, G2 to thicknesses by the value of radiation attenuation coefficient. Alternatively, the thickness of subject H may be measured by using a sensor or the like, or approximated by a model, such as a cube and an elliptical cylinder.

Incident radiation dose Io(x, y) is the dose of X-rays irradiating storable phosphor sheets IP1, IP2 when it is assumed that subject H is not present. Incident radiation dose Io(x, y) changes based on the SID, the tube voltage and an mAs value. In the present embodiment, a table showing correspondence between various kinds of SID's, tube voltages and mAs values and incident radiation dose has been stored in the storage 23. Further, incident radiation dose Io(x, y) is obtained, with reference to this table, based on the SID, the tube voltage and the mAs value.

In Expression (4), * is an operator denoting a convolution operation. Further, Sσ(T(x, y)) may be experimentally obtained based on radiography conditions. In the present embodiment, a table showing correspondence between various radiography conditions and Sσ(T(x, y)) has been stored in the storage 23, and Sσ(T(x, y)) is obtained, with reference to this table, based on radiography conditions.

Further, the image processing unit 35 calculates conversion coefficient R(x, y) for converting radiographic images G1, G2 based on scattered radiation transmittance Ts and primary radiation transmittance Tp, which are virtual grid characteristics, and distribution S(x, y) of scattered radiation contents by the following expression (6). Further, the image processing unit 35 multiplies the pixel value of each pixel in first and second radiographic image G1, G2 by conversion coefficient R(x, y) by the following expression (7), thereby obtaining first and second processed radiographic images by removing scattered radiation components from first and second radiographic images G1, G2:

$$R(x,y)=S(x,y)\times Ts+(1-S(x,y))\times Tp \quad (6); \text{ and}$$

$$Gs(x,y)=R(x,y)\times G(x,y) \quad (7).$$

Here, first and second radiographic images G1, G2 may be decomposed into plural frequency bands, and a conversion coefficient may be calculated for each of the frequency bands, and multiplication processing using the conversion coefficient may be performed for each of the frequency bands. In this case, processed first and second radiographic images Gs1, Gs2 are obtained by performing frequency synthesis on projection images of respective frequency bands multiplied by conversion coefficients.

Further, the image processing unit 35 may also perform other image processing, such as gradation correction processing, density correction processing, and frequency emphasis processing, on processed radiographic images Gs1, Gs2.

The energy subtraction processing unit 36 performs weighted subtraction processing between corresponding pixels in processed radiographic image Gs1, Gs2. Accordingly, the energy subtraction processing unit 36 generates a soft region image, in which only a soft region of subject H has been extracted, and a bone region image, in which only a bone region of subject H has been extracted. In this case, registration of processed radiographic image Gs1, Gs2 is performed by using marker images M1, M2. Specifically, registration should be performed by performing parallel translation, rotation, and enlargement or reduction on at least one of processed radiographic images Gs1, Gs2 so that marker images M1, M2 match with each other.

Next, processing performed in the embodiments of the present disclosure will be described. FIG. 7 is a flow chart showing processing performed in the embodiments of the present disclosure. First, the image obtainment unit 31 obtains first and second radiographic images G1, G2 that have been generated from first and second storable phosphor sheets IP1, IP2 by the image readout apparatus 2 (step ST1). Then, the first information obtainment unit 32 obtains first information J1 representing distance D between a detection surface of first storable phosphor sheet IP1 and a detection surface of second storable phosphor sheet IP2 (step ST2). Further, the second information obtainment unit 33 obtains second information J2 representing magnification ratio K of a second marker image of a marker 6 included in second radiographic image G2, obtained by second storable phosphor sheet IP2, with respect to a first marker image of the marker 6 included in first radiographic image G1, obtained by first storable phosphor sheet IP1 (step ST3).

Further, the distance calculation unit 34 calculates an SID based on first information J1 and second information J2 (step ST4). Then, the image processing unit 35 obtains processed radiographic images Gs1, Gs2 by performing image processing including scattered radiation removal processing on first and second radiographic image G1, G2 (step ST5). Further, the energy subtraction processing unit 36 generates a soft region image, in which only a soft region of subject H has been extracted, and a bone region image, in which only a bone region of subject H has been extracted, by performing energy subtraction processing on processed radiographic images Gs1, Gs2 (step ST6), and processing ends. The soft region image and the bone region image are displayed on the display unit 18, and provided for diagnosis.

In this way, in the embodiments of the present disclosure, the SID is calculated based on first information J1 and second information J2. Therefore, it is possible to obtain an accurate SID by using a simple and low-cost apparatus without providing a sensor or the like.

Further, it is possible to perform high-accuracy image processing using an accurate SID by performing image processing on plural first and second radiographic image G1, G2 using the obtained SID.

In the above embodiment, radiographic images of subject H are obtained by stacking two storable phosphor sheet IP1, IP2 in order to perform energy subtraction processing. It is also possible to calculate an SID by using the technique of the present application by using radiographic images obtained by long-size radiography for a long-size region, such as the whole bone (the whole spine) or the whole leg (the whole lower limb) of subject H, as a radiography target. FIG. 8 is a diagram for explaining long-size radiography. In FIG. 8, three storable phosphor sheets IP1, IP2, IP3 are used.

As illustrated in FIG. 8, three storable phosphor sheets IP1, IP2, IP3 are arranged in such a manner to be overlapped with each other during long-size radiography. Further, a marker 6 is arranged on a surface of storable phosphor sheet IP1 of storable phosphor sheets IP1, IP3, which are closer to the X-ray source 4. In long-size radiography, radiographic information about the whole body of subject H is stored and recorded on arranged three storable phosphor sheets IP1, IP2, IP3, and radiographic images G1, G2, G3 are generated by reading out radiographic image information from storable phosphor sheets IP1, IP2, IP3, respectively. Further, long-size radiographic image GL is generated by connecting generated three radiographic images G1, G2, G3 together.

Here, overlapped parts of radiographic image G1, G2 of radiographic images G1, G2, G3 obtained by long-size radiography include marker images M1, M2 of the marker 6, respectively. FIG. 9 is a diagram for explaining calculation of an SID in long-size radiography. In FIG. 9, a broken line indicates a portion of X-rays output from the X-ray source 4 that irradiates the marker 6. The range of first marker image M1 is a range in which first storable phosphor sheet IP1 and the broken line portion of the X-rays cross each other. The range of second marker image M2 is a range in which second storable phosphor sheet IP2 and the broken line portion of the X-rays cross each other. As illustrated in FIG. 9, the relationship among magnification ratio K of second marker image M2 with respect to first marker image M1, distance D between detection surfaces of storable phosphor sheets IP1, IP2 and SID is the same as the relationship about the case illustrated in FIG. 5. Therefore, also in the case that long-size radiography has been performed, the first information obtainment unit 32 obtains, as first information J1, distance D between detection surfaces of storable phosphor sheets IP1, IP2, and the second information obtainment unit 33 obtains, as second information J2, magnification ratio K of second marker image M2 with respect to first marker image M1, thereby the distance calculation unit 34 is able to calculate the SID by using the aforementioned expression (2).

In the aforementioned embodiments, the storable phosphor sheets are irradiated with X-rays that have passed through subject H, and radiographic images are obtained by reading radiographic information from the storable phosphor sheets at the image readout apparatus 2. Alternatively, radiographic images may be obtained by using radiation detectors instead of the storable phosphor sheets.

The radiation detector is able to repeat recording and readout of radiographic images. A so-called direct-type radiation detector, which generates charges by being directly irradiated with radiation, may be used. Alternatively, a so-called indirect-type radiation detector, which temporarily converts radiation into visible light, and converts the visible light into electric charge signals, may be used. Further, it is desirable to use, as a method for reading out radiographic image signals, a so-called TFT readout method, in which radiographic image signals are read out by ON/OFF of a TFT (thin film transistor) switch, or a so-called light readout method, in which radiographic image signals are read out by irradiation with readout light. However, the method is not limited to these methods, and other methods may be used.

Here, also in the case that the radiation detectors are used, an SID is calculable in a similar manner to the aforementioned embodiments. Here, first and second radiation detectors DR1, DR2 are used instead of first and second storable phosphor sheets IP1, IP2, used in the aforementioned embodiments, and first and second radiographic images G1, G2 are obtained from first and second radiation detectors DR1, DR2, respectively. The first information obtainment unit 32 obtains first information J1 representing a distance between a detection surface of first radiation detector DR1 and a detection surface of second radiation detector DR2. Also in this case, the thicknesses of first and second radiation detectors DR1, DR2, and the thickness of a filter 5 are already known. Therefore, distance D is a value obtained by adding the thickness of the filter 5 to the thickness of first radiation detector DR1. Meanwhile, the second information obtainment unit 33 obtains second information J2, which is a magnification ratio of a second marker image of a marker 6 included in second radiographic image G2, obtained by second radiation detector DR2, with respect to a first marker image of the marker 6 included in first radiographic image G1, obtained by first radiation detector DR1. Further, the distance calculation unit 34 is able to calculate an SID based on first information J1 and second information J2 by using the abovementioned expression (2).

In the aforementioned embodiments, plural markers 6 are used. Alternatively, only one marker 6 may be used.

Further, in the aforementioned embodiments, a marker 6 made of metal that does not pass X-rays is used. Alternatively, a marker 6 made of material, such as metal or resin, that passes X-rays may be used as long as it is possible to make a marker image included in a radiographic image in such a manner to be distinguishable from a subject image.

Further, in the aforementioned embodiments, a marker 6 is placed in close contact with a storable phosphor sheet that is closer to the X-ray source 4. Alternatively, the marker 6 may be arranged away from the storable phosphor sheet. For example, the marker 6 may be arranged, for example, on subject H.

Further, in the aforementioned embodiments, radiography is performed by arranging two storable phosphor sheets in such a manner to be overlapped with each other with respect to the optical axis of X-rays. Alternatively, radiography may be performed by arranging three or more storable phosphor sheets in such a manner to be overlapped with each other. Also in that case, an SID is calculable in a similar manner to the aforementioned embodiments. In this case, distance D between a detection surface of a storable phosphor sheet closest to the X-ray source and a detection surface of one of second closest and later storable phosphor sheets, and magnification ratio K of a marker included in a radiographic image obtained from the one of the storable phosphor sheets used in obtainment of the aforementioned distance D with respect to a marker image included in a radiographic image obtained from the storable phosphor sheet closest to the X-ray source are obtained, and used to calculate an SID.

In the aforementioned embodiments, the technique disclosed in Patent Document 1 is used, as scattered radiation removal processing, but an arbitrary technique, such as a technique disclosed in Patent Document 2, may be used.

In the aforementioned embodiments, scattered radiation removal processing is performed as processing using an SID, but other image processing using an SID may be performed.

What is claimed is:

1. A radiographic image processing apparatus comprising:
   an image obtainment unit that obtains a plurality of radiographic images generated by arranging a plurality of detection unit that detect radiation that has been output from a radiation source and passed through a subject in such a manner that at least portions of the plurality of detection unit are overlapped with each other in an irradiation direction of the radiation, and by arranging at least one marker at a position to be detected by the plurality of detection unit, and by detecting the radiation that has passed through the subject and the marker by each of the plurality of detection unit;
   a first information obtainment unit that obtains first information representing a distance between a detection surface of a first detection unit located closest to the radiation source among the plurality of detection unit and a detection surface of a second detection unit other than the first detection unit among the plurality of detection unit;
   a second information obtainment unit that obtains second information representing a magnification ratio of a second marker image of the at least one marker included in a second radiographic image obtained by the second detection unit with respect to a first marker image of the at least one marker included in a first radiographic image obtained by the first detection unit;
   a distance calculation unit that calculates, based on the first information and the second information, a radiation-source-to-image-surface distance, which is a distance between the radiation source and the detection surface of the first detection unit;
   an image processing unit that performs scattered radiation removal processing on at least one of the plurality of radiographic images by using the radiation-source-to-image-surface distance; and
   an energy subtraction processing unit that performs energy subtraction processing on the plurality of radiographic images which include the at least one radiographic image on which the scattered radiation removal processing is performed.

2. The radiographic image processing apparatus, as defined in claim 1, wherein the second information obtainment unit obtains, as the second information, an average value of the magnification ratio obtained for each marker in the case that the arranged at least one marker is a plurality of markers.

3. A radiographic image processing method comprising:
   obtaining a plurality of radiographic images generated by arranging a plurality of detection unit that detect radiation that has been output from a radiation source and passed through a subject in such a manner that at least portions of the plurality of detection unit are overlapped with each other in an irradiation direction of the radiation, and by arranging at least one marker at a position to be detected by the plurality of detection unit, and by detecting the radiation that has passed through the subject and the marker by each of the plurality of detection unit;
   obtaining first information representing a distance between a detection surface of a first detection unit located closest to the radiation source among the plurality of detection unit and a detection surface of a second detection unit other than the first detection unit among the plurality of detection unit;
   obtaining second information representing a magnification ratio of a second marker image of the at least one marker included in a second radiographic image obtained by the second detection unit with respect to a first marker image of the at least one marker included in a first radiographic image obtained by the first detection unit;
   calculating, based on the first information and the second information, a radiation-source-to-image-surface distance, which is a distance between the radiation source and the detection surface of the first detection unit;

performing scattered radiation removal processing on at least one of the plurality of radiographic images by using the radiation-source-to-image-surface distance; and performing energy subtraction processing on the plurality of radiographic images which include the at least one radiographic image on which the scattered radiation removal processing is performed.

4. A non-transitory recording medium having recorded therein a radiographic image processing program that causes a computer to execute:

a procedure that obtains a plurality of radiographic images generated by arranging a plurality of detection unit that detect radiation that has been output from a radiation source and passed through a subject in such a manner that at least portions of the plurality of detection unit are overlapped with each other in an irradiation direction of the radiation, and by arranging at least one marker at a position to be detected by the plurality of detection unit, and by detecting the radiation that has passed through the subject and the marker by each of the plurality of detection unit;

a procedure that obtains first information representing a distance between a detection surface of a first detection unit located closest to the radiation source among the plurality of detection unit and a detection surface of a second detection unit other than the first detection unit among the plurality of detection unit;

a procedure that obtains second information representing a magnification ratio of a second marker image of the at least one marker included in a second radiographic image obtained by the second detection unit with respect to a first marker image of the at least one marker included in a first radiographic image obtained by the first detection unit;

a procedure that calculates, based on the first information and the second information, a radiation-source-to-image-surface distance, which is a distance between the radiation source and the detection surface of the first detection unit;

a procedure that performs scattered radiation removal processing on at least one of the plurality of radiographic images by using the radiation-source-to-image-surface distance; and a procedure that performs energy subtraction processing on the plurality of radiographic images which include the at least one radiographic image on which the scattered radiation removal processing is performed.

* * * * *